(12) United States Patent
Berestov

(10) Patent No.: US 6,690,762 B1
(45) Date of Patent: Feb. 10, 2004

(54) N-DIMENSIONAL DATA ENCODING OF PROJECTED OR REFLECTED DATA

(75) Inventor: Alexander L. Berestov, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 95 days.

(21) Appl. No.: 09/796,668

(22) Filed: Feb. 28, 2001

(51) Int. Cl.$^7$ ............................................. G01N 23/04
(52) U.S. Cl. ............................. 378/62; 378/4; 378/901
(58) Field of Search ........................ 348/113; 707/101; 345/426; 430/22; 378/901, 62, 4; 382/128, 132

(56) References Cited

U.S. PATENT DOCUMENTS

| | | | | |
|---|---|---|---|---|
| 5,778,374 A | * | 7/1998 | Dang et al. ................... | 707/101 |
| 6,222,583 B1 | * | 4/2001 | Matsumura et al. .......... | 348/113 |

OTHER PUBLICATIONS

Paul Bourke, Vision–3D, 1989, Version 1.7, pp. 1–49, http://astronomy.swin.edu.au/~pbourke/modelling/vision3D.*
Center for Environmental Applications of Remote Sensing, What is a Geographic Information System?., Summer 1999, pp. 1–10.*
Minutes from 3D DICOM Work Group—WG 17, Diagnostic Imaging an Therapy Systems Division, Feb. 25, 1999.
White paper entitled "3D File Format Example for WG12 and WG17", C. Deforge, Siemens Medical Systems, Inc., Ultrasound Group, May 11, 1999.
White paper entitled "Node–based Approach to N–Dimensional Data Set Representation", D. Sluis, May 17, 1999.
White paper entitled "Requirements for N–dimensional Data Sets", May 17, 1999 (2 pages).
White paper entitled "Requirements for N–Dimensional Data Sets", B. Hemminger, May 17, 1999 (3 pages).
White paper entitled "Conceptual encoding of N–dimensional data sets", A. Berestov (6 pages).
Minutes from 3D DICOM Work Group—WG 17, Diagnostic Imaging an Therapy Systems Division, May 18–19, 1999.

(List continued on next page.)

Primary Examiner—Matthew C. Bella
Assistant Examiner—Linzy McCartney
(74) Attorney, Agent, or Firm—Fitzpatrick, Cella, Harper & Scinto

(57) ABSTRACT

A system, method, and computer-readable medium formats imaging data associated with an object in an n-dimensional file format. Once two-dimensional imaging ray data (projected or reflected data) is acquired, it is saved into an n-dimensional format (500) along with data describing the reference point and focal point of the image. A preferred format (500) comprises a file header (505), a header of the reference point, coordinates of the focal point field, a transformation field, and dimension sub-headers (550, 560). The system comprises a data acquisition module (612), a data storage module (630), a data reading module (640), and a data processing module (610) for formatting the data, reading the formatted data, and fusing the formatted data with other data sets, such as three-dimensional data.

19 Claims, 10 Drawing Sheets

OTHER PUBLICATIONS

White paper entitled "Cartesian and Non Cartesian Representation of N–Dimensional Data Sets", A. Berestov, Jul. 21, 1999.

Minutes from DICOM WG17 (3D), DICOM Standards Committee, Sep. 16, 1999.

Minutes from 3D DICOM Work Group—WG 17, Diagnostic Imaging an Therapy Systems Division, May 8–9, 2000.

White paper entitled "N–dimensional encoding of the projected and reflected data", A. Berestov, Apr. 7, 2000.

Minutes from 3D DICOM Work Group—WG 17, Diagnostic Imaging an Therapy Systems Division, Nov. 29, Dec. 1, 2000.

White paper entitled "N–dimensional representation of topographic data", A. Berestov, Feb. 13, 2001.

Minutes from 3D DICOM Work Group—WG 17, Mar. 2, 2001.

Berestov, Alexander L., "Multidimensional Data Encoding", Application No. 09/636,298, filed Aug. 10, 2000.

Berestov, Alexander L., "Non–Cartesian Representation", Application No. 09/618,200, filed Jul. 18, 2000.

* cited by examiner

File Header

| 1sT Byte (file identifier) | 2nd Byte (file identifier and/or format identifier) | 3rd Byte (format identifier) | 4th Byte (format identifier) | 5th Byte (data type identifier) | 6th Byte (number of dimensions identifier) |
|---|---|---|---|---|---|
| | | | | | |

FIG. 10

N-DIMENSIONAL DATA ENCODING OF PROJECTED OR REFLECTED DATA

RELATED APPLICATIONS

The present application is related to commonly-assigned U.S. patent application Ser. No. 09/618,200, entitled "Non-Cartesian Representation" filed Jul. 18, 2000, by Alexander Berestov, the entire contents of which are hereby incorporated by reference.

The present application is also related to commonly-assigned U.S. patent application Ser. No. 09/636,298, entitled "Multidimensional Data Encoding," filed Aug. 10, 2000, by Alexander Berestov, the entire contents of which are hereby incorporated by reference.

BACKGROUND OF THE INVENTION

1. Field of the Invention

The present invention relates generally to the field of storing image data in a file format and more particularly, to a file format and method for storing projected or reflected image data.

2. Description of Background Art

There are a variety of data analysis problems for which different types of data are collected and later analyzed. In the medical field, for example, two or more types of image data may be collected, such as computerized tomography (CT) scan data, ultrasound image data, x-ray image data, infrared image data, and photographic data. Each image technique may reveal different features or aspects of a medical condition. Consequently, it is desirable to have the capability to combine or compare aspects of the different data sets at particular locations in the object, to form fused three-dimensional images from the combined data sets, and to manipulate the data sets in a variety of different ways.

Several factors may limit the ability to effectively combine different types of data into overlapping or fused images. These include registration errors and image rendering errors. Registration errors may occur because the data is collected on different types of imaging machines from different positions. Registration errors, may, for example, result in an offset in two rendered three-dimensional images, creating a registration error in the fused image. Rendering errors may occur because the collected two-dimensional images lack sufficient information to form accurate three-dimensional images from the data set of collected two-dimensional images.

Registration and rendering errors are a particular problem for collected projected and reflected image data. Projected image data corresponds to two-dimensional images collected as a consequence of passing an imaging ray (e.g., x-rays) through an object and onto a sensor plate. Reflected data corresponds to two-dimensional images collected from image rays (e.g., light rays) reflecting from an object and collected on a sensor plate. Image rendering of two-dimensional projected or reflected data sets is a problem because each individual two-dimensional image lacks sufficient depth information to uniquely establish the location of the object being imaged. Conventional image rendering techniques use several images to calculate a depth map. However, this imposes geometric constraints on the images used to calculate depth data. Additionally, the data format of the rendered data may be different than the other types of data, complicating the problem of registering and fusing the image data with other types of data, such as CT data.

Therefore, there is a need for a new technique of collecting and storing projected or reflected data into a format that is compatible with different coordinate transformations and fusing the projected or reflected data with different types of data.

DISCLOSURE OF INVENTION

The present invention is a system, method, and computer-readable medium for saving multidimensional data that includes two-dimensional imaging ray data, such as projected or reflected data.

The system includes a data acquisition module (612) for acquiring a first data set of imaging ray images of the object; a formatting module (602) in communication with the data acquisition module (612) and configured to format the data set into an n-dimensional format (500) comprising: a reference point value field, a transformation field, a focal point value field, a type of the coordinate system, and at least one dimension for storing image data; and a storage module (632) in communication with the formatting module (602) and configured to store the formatted data. In a preferred embodiment, two dimensions of the format are used for storing two dimensional image data.

The method includes the steps of acquiring a first data set comprised of a plurality of two dimensional imaging ray images of the object; formatting each of the two-dimensional imaging ray images of the first data set into an n-dimensional format (500) having a file header, a reference point header, coordinates of the focal point field, and at least one dimension for storing image data; and storing the resulting formatted data.

The computer-readable medium includes a computer program comprising: a data acquisition module (612) for acquiring a first data set of imaging ray images; a formatting module (602) in communication with the data acquisition module (612) and configured to format the first data set into a file structure (500), the file structure comprising: a file header, a header of the reference point and a focal point field; and a storage module in communication with the formatting module and configured to store the formatted data sets in n-dimensional format.

BRIEF DESCRIPTION OF THE DRAWINGS

The above and other more detailed and specific objects and features of the present invention are more fully disclosed in the following description, reference being had to the accompanying drawings, in which:

FIG. 10 is an illustration of one embodiment of a file header structure for the file format of FIG. 5.

DETAILED DESCRIPTION OF THE PREFERRED EMBODIMENTS

The present invention relates to the manipulation and formatting of data sets in which at least one data set may comprise a reflected or projected data set, such as two-dimensional x-ray images or two-dimensional optical images. As used hereinafter in this application, the term "imaging ray image" includes two-dimensional images arising from imaging rays interacting with an object and collected on a sensor surface. Two-dimensional imaging ray data includes data sets corresponding to imaging rays passing through the body of an object that are collected along a two-dimensional sensor surface ("projected data"). Two-dimensional imaging ray data also includes imaging rays reflected from the surface or sub-surface of an object ("reflected data") that are collected along a two-dimensional sensor surface. Projected and reflected data sets typically arise from electromagnetic radiation passing through or reflected from an object that strikes a sensor plate. However, projected and reflected data sets may also be mathematically created from other data sets as well.

Figure 1A:
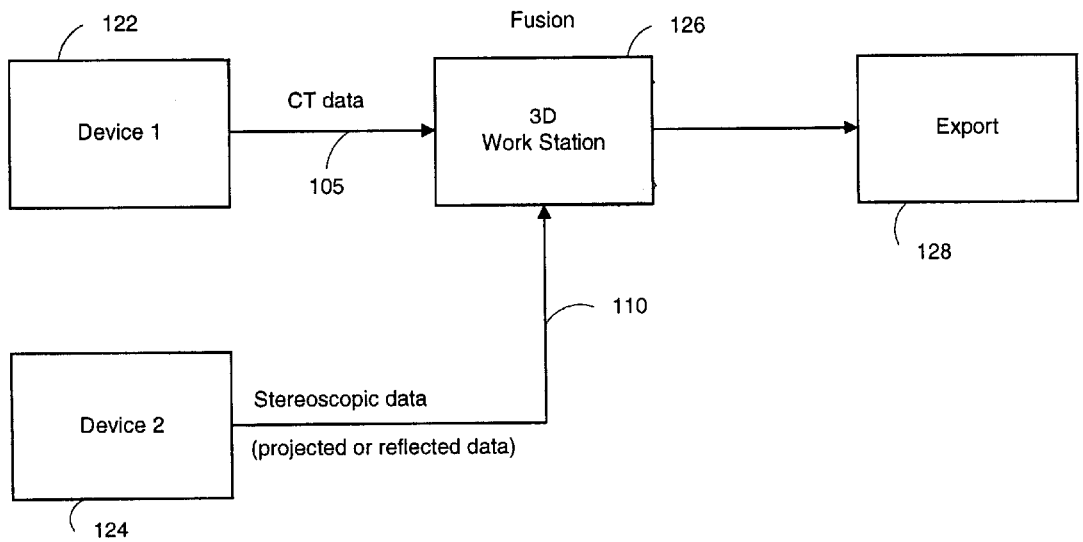
FIG. 1A is an illustration of a system for formatting data sets of different types into a single n-dimensional format.

With reference to FIG. 1A, a computer system 126, according to one embodiment of the present invention, can manipulate and format, for example, data set 105 from a first device 122 such as computerized tomography (CT) data, magnetic resonance (MR) detector data, or ultrasound detector data. Note that data 105 can be acquired in a variety of different coordinate systems depending upon the apparatus of first device 122.

The first data set 105 from a first device 122, such as CT data, may be collected and input into a workstation 126 as a first source of 3-D data. A second data set 110 may be collected from a second device 124 that comprises imaging ray data (projected or reflected data), such as x-ray data or optical data. The projected or reflected data may be input to the workstation in the form of two-dimensional images, such as two dimensional images recorded as an array of pixels on a sensor plate.

Note that accurate registration of first data set 105 and second data set 110 is desired. Additionally, since second data set 110 comprises two-dimensional images, data set 110 typically needs to be transformed ("rendered") into images that may be mapped onto the two-dimensional or three-dimensional images of first data set 105. It is desirable that software on the workstation 126 matches the data set 110 exported by the second device 124 and calculates a depth map, since this permits new views (e.g., three dimensional images) to be calculated from data set 110 using conventional image rendering techniques. Then the workstation 126 may calculate a transformation that registers one data set 105 to the other 110, thereby facilitating the creation of a fused three-dimensional data.

Figure 1B:
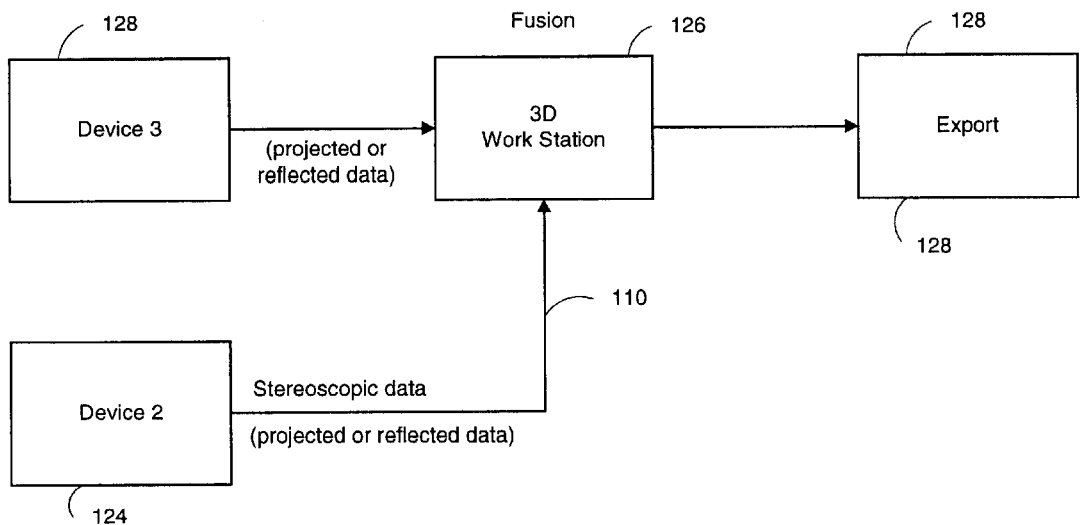
FIG. 1B is an illustration of an alternate embodiment of the system of FIG. 1A.

The fused data file is preferably in an n-dimensional format having sufficient dimensionality to have data fields for the different potential data types of data sets 105 and 110. The workstation then exports 128 the fused data 128 or stores it on a local storage medium. FIG. 1B shows a variation of the apparatus of FIG. 1A in which both data sets 150, 110 are from devices 124 and 128 that acquire projected or reflected data.

Figure 2A:
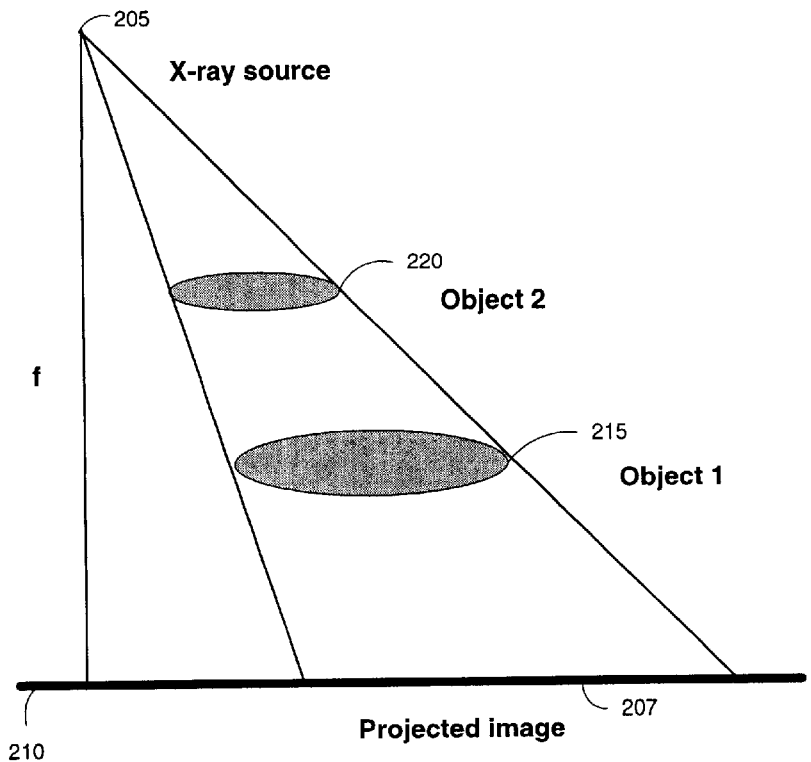
FIG. 2A is an illustrative diagram of a projected image geometry.
Figure 2B:
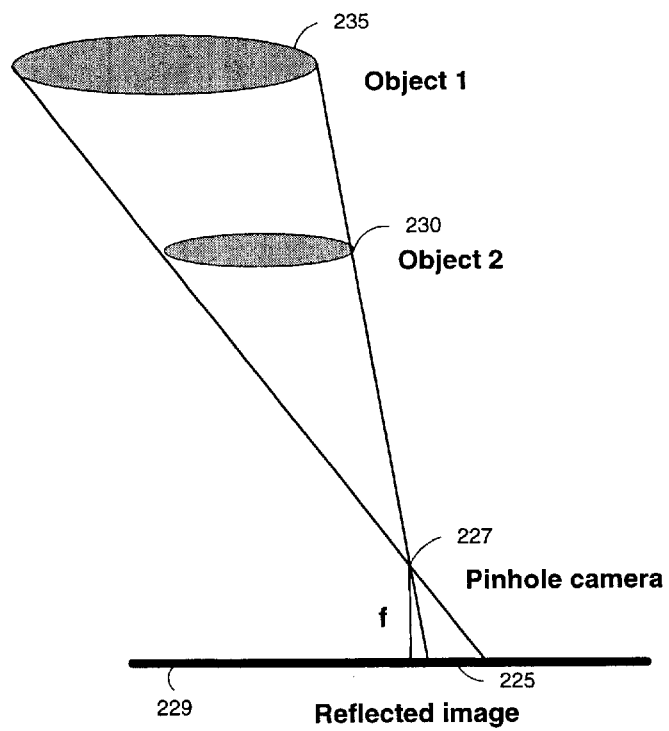
FIG. 2B is an illustrative diagram of a reflected image geometry.

In accord with the present invention, sensor location data and focal point data are acquired for each two-dimensional projected or reflected image to facilitate forming a depth map for the projected or reflected data. FIG. 2A shows an illustrative diagram of a projected image projected from an x-ray source. X-ray source 205 creates a projected image 207 of an object on a two-dimensional surface 210. As shown in FIG. 2A, a single two-dimensional projected image 207 recorded on two-dimensional surface 210 may arise from an object 215 or an object 220 located at different distances from the projected image surface 210. FIG. 2B shows an illustrative diagram of a reflected image of an optical camera. A reflected image 225 collected on two-dimensional surface 229 via a camera 227 may be produced by an object 230 or an object 235 located different distances from camera 213. For both projected and reflected data, a single two-dimensional image lacks depth information.

Figure 3:
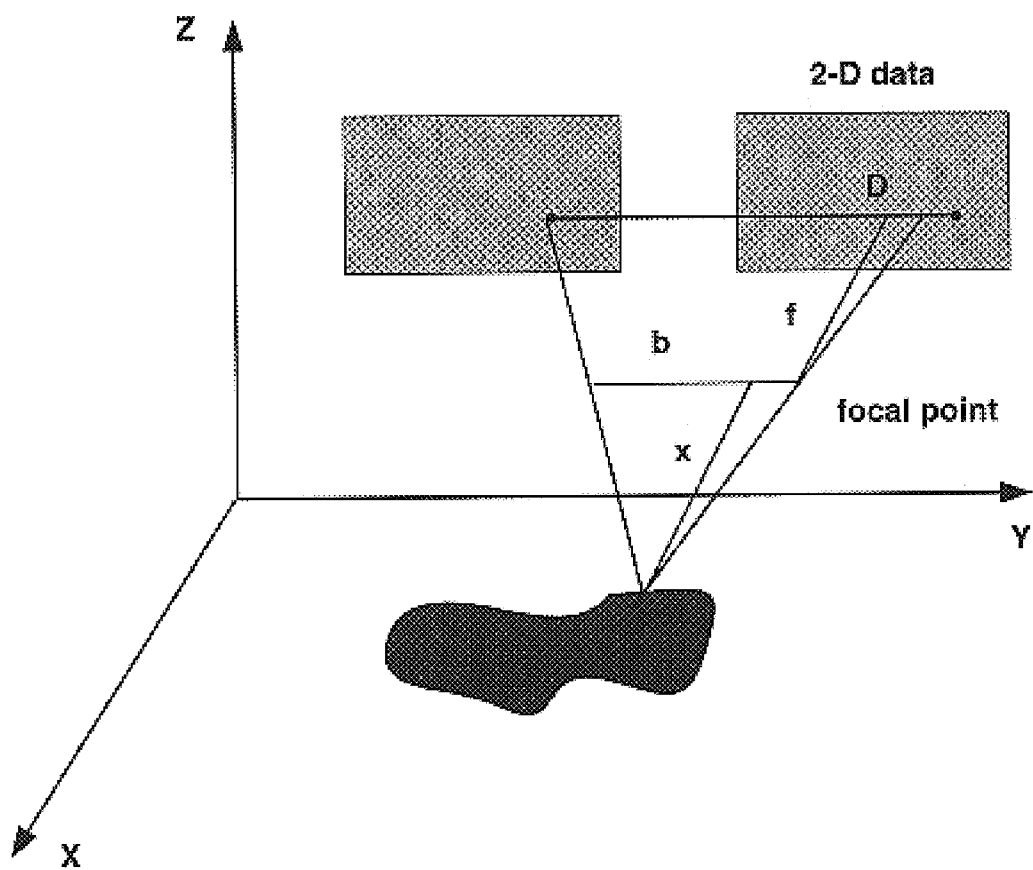
FIG. 3 is an illustrative diagram of a method of using focal point data to form a depth map for two-dimensional images.

Referring again to the two-dimensional imaging ray data (projected and reflected data images of FIGS. 2A and 2B, a depth map may be calculated if the locations of the image (the sensor location) and the focal point, $f_p$, of the image are known. This is because the focal point information provides information that facilitates forming correspondences between points in two or more images of the object. For the case of optical images, knowledge of the focal point of the image at the reference point (sensor location) of the image permits a disparity field to be calculated. The disparity field is the displacement of corresponding points along epipolar lines. FIG. 3 illustrates the geometry for two optical images taken from parallel cameras. For the special case of two cameras in parallel, the disparity is inversely proportional to the distance from the object to the base line. This can be expressed mathematically as: $D=fb/x$, where D is the disparity, f is the focal length of the cameras, b is the distance between the cameras, and x is the distance from the object to the baseline (focal length). If the location of the sensor plate and the focal points are available, points in two images can be matched and the coordinates of each point calculated. For the case of x-ray images, the projected image contains information about all the points along the ray, i.e., the x-ray interacts with the entire object along its path. For projected x-ray images, depth information may be extracted by combining several images and blurring all the planes across the object except the selected one using tomosynthesis techniques. Knowledge of the focal point of the projected x-ray image facilitates combining several images and blurring all the planes across the object except the selected one.

A variety of techniques may thus be used to extract depth information for forming new views from collected two-dimensional imaging ray data (projected or reflected data sets) as long as the location of each data set on the sensor plate and the associated focal point of each image is stored with the data set, since this permits depth information to be calculated from the stored data set. The depth map, in turn, permits reconstruction of the three-dimensional image and the formation of two-dimensional images from different viewpoints.

Figure 4:
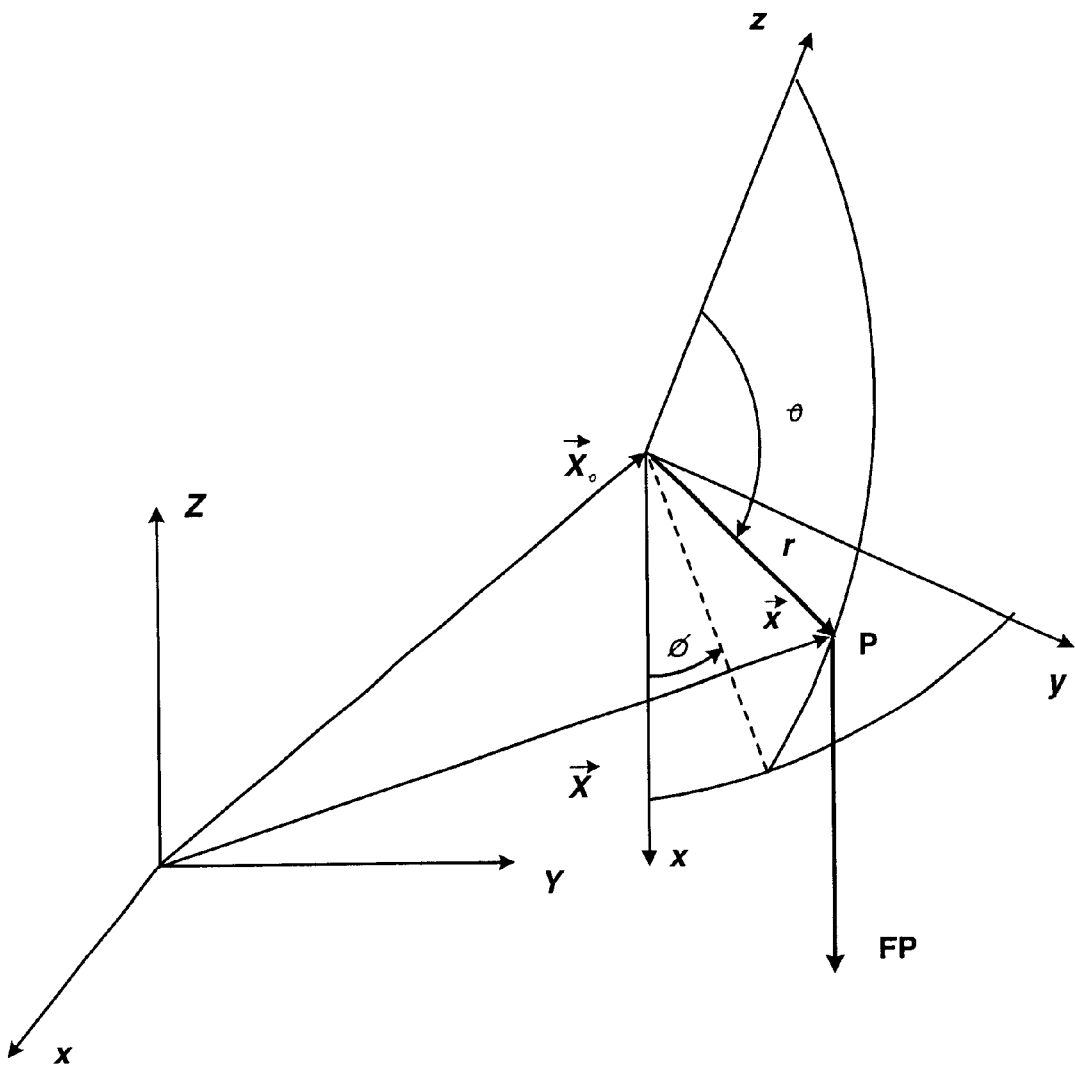
FIG. 4 illustrates the coordinate transformation to a sensor position and the corresponding position of a focal point.

Referring to FIG. 4, a reference location point of an image may be stored as coordinate data, such as X, Y, and Z coordinate positions at the sensor plate. The coordinate data may be stored in a local coordinate system, such as a Cartesian coordinate system or as a non-Cartesian coordinate system. The focal point, $f_p$, is preferably stored in the same local coordinate system.

Thus, in accord with the present invention, for each two-dimensional projected or reflected image, the locations of the sensor position and the focal point are recorded. A suitable format facilitates storing focal point data along with the two-dimensional pixel data of two-dimensional imaging ray data (projected or reflected data). In addition to storing the desired data, a preferred format also facilitates collecting data sets 105 and 110 of different types and/or in different coordinate systems, thereby facilitating fusing data sets in workstation 126.

Figure 5:
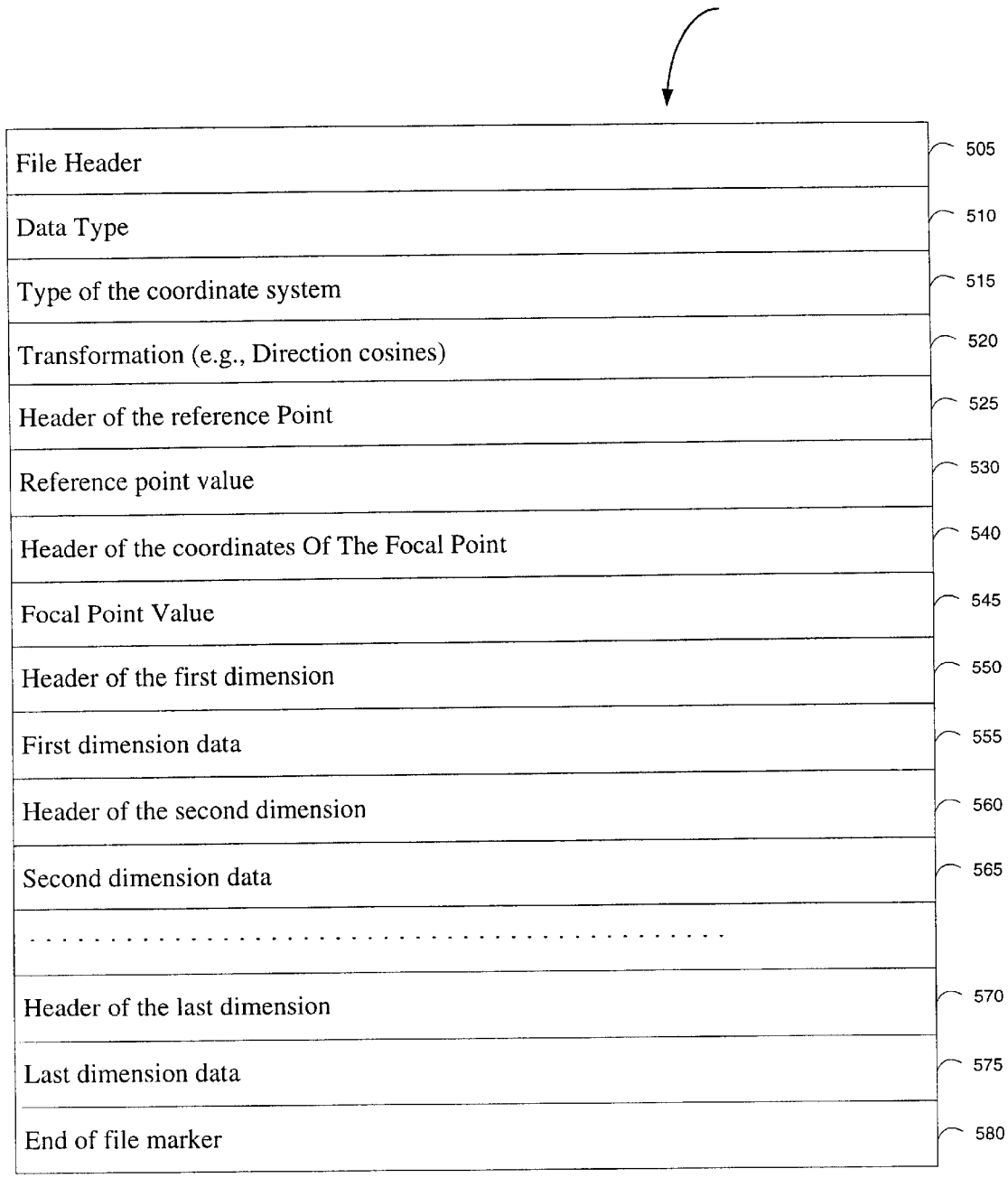
FIG. 5 is an illustrative diagram of the physical format of an n-dimensional data structure in accord with the present invention.

FIG. 5 is an embodiment of a preferred n-dimensional format 500 for storing n-dimensional data sets that include the focal point data, sensor location, and preferably at least two 2-dimensional fields for storing two-dimensional pixel data. The format is n-dimensional in that there is a header for each data dimension and a corresponding field for storing data for each dimension. This format is particularly useful for storing two-dimensional pixel data, since it provides a convenient format for storing pixel data of the image along with the sensor position and focal point data. In a preferred embodiment, two-dimensional pixel data is stored in two separate dimensions of format 500, although it will be understood that two-dimensional pixel data may be stored in other ways that are consistent with the n-dimensional nature of format 500.

A focal point coordinate header 540 and corresponding field 545 are included to store the coordinates of the focal point of the image. It will be understood that a single focal point field 545 without a header 540 may also be used if the focal point field is placed at a location in the format that is fixed relative to another element, such as placing the focal point value in a field immediately below the reference point value 530. Note that for data types, such as CT data, that do not have focal point data, the focal point value 545 may be left at a default value, i.e., data format 500 may also be used for other types of data besides projected or reflected data sets by indicating that the data type 510 is one for which there is no focal point data. Thus, a format that has a default value for the focal point coordinates or which omits the focal point coordinate field is a special case of format 500. Format 500 may thus be used for storing other types of data besides projected and reflected data sets. Note also that additional dimensions of the format may also be reserved for storing other types of data, such as CT data. Format 500 is thus compatible with storing other types of data besides projected or reflected data sets.

The format 500 includes a file header 505, and a data type field 510. Data type field 510 can be used to indicate whether the data is projected data, reflected data type, or another data type, as described below in more detail. With reference to FIG. 10, the file header identifies the file as an n-dimensional file and, as described below, includes a format identifier, and a number of dimensions identifier.

The format 500 also preferably includes a type of the coordinate system field 515. The type of the coordinate system field 515 provides information that allows processing systems to convert between local Cartesian and non-Cartesian coordinate systems.

The header of the reference point 525 comes after the file header 505. The header of the reference point 525 has a block (field) 530 that contains the coordinates of the reference point in multidimensional space. For projected and reflected data, the reference point corresponds to a sensor location at which the image is observed.

The value of the reference point 530 is defined by the type of the data from the N-dimensional file header 505. In the case of a real number, the size is equal to 4 bytes. In the case of a double type number, it is equal to 8 bytes.

The format 500 includes headers of each dimension (referred to as subheaders) and data fields for each dimension. The header of the first dimension 550 (a first subheader) has a structure that is analogous to the structure of the reference point header. In particular, it defines the coordinates of the first vector in multidimensional vector space. The data along this vector are one-dimensional. The number of the points N(1) could be read from the last four bytes of the header. In order to obtain this information, data can be skipped.

The type of the data from the N-dimensional file header defines the size of every datum in this field. The first datum in the row is located in the previous data block. This means that the row begins with the reference point, and it is not necessary to write it twice.

The header of the second dimension 560 (a second subheader) has an identical structure as the header of the first dimension 550, except that every new data buffer represents data in a new dimension. In particular, it defines the coordinates of the second vector in multidimensional vector space. The data along this vector are two-dimensional. The number of the points N(2) could be read from the last four bytes of the header. In order to obtain this information, data can be skipped. Second dimension data are $\{N(2)-1\}$ rows along the second vector and the data from the previous data blocks compose the first row.

The end of file marker 580 is the relative file address of the first byte past the end of all N-dimensional data. It is used to determine if a file has been accidentally truncated. In addition, it is used as an address where file memory allocation can occur if the information in headers is not used.

The format 500 also preferably includes a transformation field 520. The transformation field 520 provides information for transforming between the local Cartesian coordinate system and a global coordinate system.

In a preferred embodiment, the transformation field is a direction cosines field. Referring again to FIG. 4, FIG. 4 illustrates the relationship between a global (or reference) coordinate system (x, Y Z) and a local coordinate system (x,y,z) or (θ,φ,r). By definition, the global coordinate system is preferably a Cartesian coordinate system. The local coordinate system can be either Cartesian or non-Cartesian depending on the nature of the data.

When both systems are Cartesian, transformation includes only rotation and translation:

$$X = t_{11}x + t_{12}y + t_{13}z + X_0, \quad (1)$$
$$Y = t_{21}x + t_{22}y + t_{23}z + Y_0, \quad \text{or} \quad \vec{X} = T\vec{x} + \vec{X}_0.$$
$$Z = t_{31}x + t_{32}y + t_{33}z + Y_0,$$

Here $\vec{X}$ is the position vector in the global coordinate system, x is the position vector in the local coordinate system, and $\vec{X}_0$ is the position vector of the local coordinate system origin in the global coordinate system (translation vector). T is the rotation matrix. Its elements are direction cosines of the local coordinate axes in the global coordinate system:

axis Ox has direction cosines $t_{11},t_{21},t_{31}$,
axis Oy has direction cosines $t_{12},t_{22},t_{32}$,
axis Oz has direction cosines $t_{13},t_{23},t_{33}$.

Direction cosines are the cosines of the direction angles with respect to the X-axis, Y-axis, and Z-axis respectively:

$$\sum_{i=1}^{3} t_{ij}^2 = 1, \quad j = 1, 2, 3. \quad (2)$$

Equation (2) allows storing just two of the direction cosines and calculating the third one when it is necessary.
One embodiment stores the rotation matrix and translation vector together and stores the local data set separately.

When the local coordinate system is non-Cartesian, an embodiment of the present invention utilizes the relationship between the non-Cartesian and the Cartesian coordinate systems. For example, spherical coordinates relate to Cartesian coordinates as follows:

$$\begin{aligned} x &= z_l \sin x_l \cos y_l, & x_l &= \theta, \\ y &= z_l \sin x_l \sin y_l, & y_l &= \phi, \\ z &= z_l \cos x_l, & z_l &= r. \end{aligned} \quad (3)$$

These Cartesian coordinates can be considered as local Cartesian coordinates, so that for every local coordinate system $(x_l, y_l, z_l)$ there exists a unique local Cartesian coordinate system $(x,y,z)$. One embodiment of a file format according to the present invention stores the rotation matrix and translation vector for making the transformation between the global Cartesian coordinate system and the local Cartesian coordinate system in order to allow transformation between the coordinate systems.

Note that the local Coordinate system can be either Cartesian or non-Cartesian. When the local coordinate system coincides with the local Cartesian coordinate system, equation (3) becomes:

$$x=x_l,$$
$$y=y_l,$$
$$z=z_l. \quad (4)$$

The local Cartesian coordinate system of one data set can coincide with the local coordinate system of another data set. In this case, a format according to one embodiment of the invention records the relationship between the two coordinate systems.

The reference point header and value fields provide information for constructing the translation vector of equation (1). Thus, these fields allow for the transformation of data between the local Cartesian coordinate system and the global coordinate system. With respect to equation (2), the direction cosines field can include 6 or 9 direction cosines. The coordinate of the focal point is preferably stored in the local coordinate system similar to the reference point value. Thus, the coordinates of the focal point may be in Cartesian or non-Cartesian coordinates depending upon the local coordinate system.

The format 500 can locate the type of the coordinate system field and the direction cosine field before or after the reference point section that defines translation. Indeed, the structure of the format can take a number of variations, as will be obvious to those of skill in the art.

With respect to the type of coordinate system field 505, it is possible to describe nearly any kind of coordinate system type. However, most applications use predefined types that are supported by their compiler.

These coordinate system types can be C-like data types that are generally supported by the hardware of the machine. Several examples of data types are signed character, unsigned character, short, unsigned short, integer, long, float, double, etc.

The length of the type of coordinate system field 515 can be one byte. In this case, 256 different coordinate systems could be predefined.

For every coordinate system type supported by the format, the system defines the relationship of the local coordinates to a local Cartesian coordinate system. A system user can also define a coordinate system type and its associated relationship with a local Cartesian coordinate system.

As an illustrative example of a reflected data image, a single photograph (a single image of a reflected data set) could be represented in a coordinate system similar to equation 1:

$$x = t11X + t12Y + t13Z + x0$$

$$y = t11X + t22Y + t23Z + y0$$

$$z = t11X + t32Y + t33Z + z0$$

Where tij are the direction cosines; x, y, and z are the global coordinates; and x0, y0, and z0 are the global coordinates of the origin of the local coordinate system. The pixel data may be stored in two of the dimensional fields, such as fields 555 and 565, of the format. As an illustrative example, the voxel size could correspond to pixels each having a 24 bit value. The dataset axis, in a first dimension, Y, could have units of mm, a size of 512 (Y pixels), and a sample interval of 0.05 mm (between pixels). The data set axis x in a a second dimension could have units of mm, a size of 512 (X pixels), and an interval of 0.05 mm (between pixels). Additionally, the dataset would include the coordinates X1, Y1, and Z1 of the focal point in the local coordinate system. The field for storing the coordinates of the focal point would preferably consist of 12 bytes. The coordinates are defined as a real value, although it is possible to define the coordinates of the focal point as double or integer.

Figure 6:
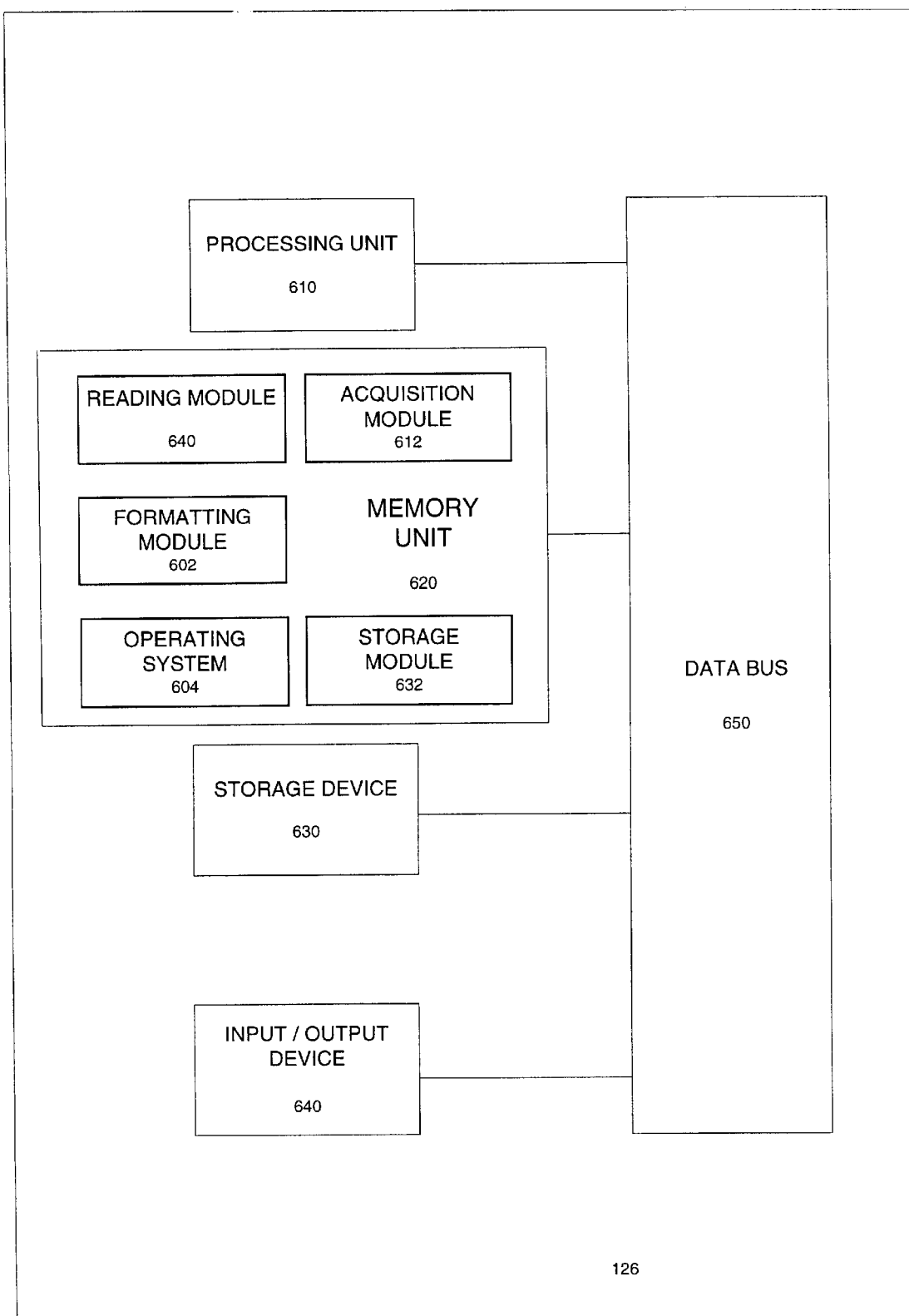
FIG. 6 is a block diagram of the workstation of FIG. 1A.

Format 500 is compatible with an automated system for formatting projected or reflected data sets, automated systems for reading the formatted data, and automated systems for fusing the formatted data in a workstation. With reference to FIG. 6, one embodiment of the computer system 126 for formatting, reading, and fusing data includes a central processing unit 610, a memory unit 620, a storage device unit 630, and an input device unit 640, all of which communicate via data bus unit 650. The memory unit 620 can be a dynamic random access memory, a static random access memory, or the like.

The storage device 630 is a conventional storage device, for example, a magnetic disk drive, or a solid-state disk. The input device 640 is a conventional input device connection. The system bus 650 is a conventional system bus, for example, a peripheral module interconnect, or a fire wire. The memory unit 620 includes an operating system 604, a data acquisition module 612, a formatting module 604, and a storage module 632.

Programs within the memory unit 620 utilize the relationship between a global (or reference) coordinate system and a local coordinate system to provide a single format for data sets. The data sets can be described using different coordinate systems.

Referring to FIG. 6, the data acquisition module 612 is configured to acquire data that extends in a plurality of dimensions, which can include more than the two dimensions required to store a two-dimensional image. A dimension is defined as any measurable extent, such as length or width. In the present invention, a vector in multidimensional data space describes every new dimension. This vector is defined in three-dimensional Euclidean space, time, sample space, etc. Each regularly or irregularly spaced data set starts with a reference point. Coordinates of this point must be given in some basic coordinate system. Given this structure, the data acquisition module 612 acquires regularly or irregularly spaced data.

The formatting module 602 writes data into format 500. As a result of the formatting process, the data is transformed into a physical format 500.

Referring again to FIG. 6, the storage module 632 stores data. After the formatting module 602 formats the multidimensional data in format 500, the data, which is currently residing in memory 620, can be stored in a storage device 630, a memory 620, a permanent storage medium, such as a disk, or a tape.

The reading module 640 performs extraction of information from a file using a file header to ascertain the location of subheaders of interest. The file header structure is shown in FIG. 10. The file header consists of a series of blocks. The data storage module 632 stores the type of the data and the number of dimensions in the last two bytes of the file header. The size of every dimension is in the last byte of the corresponding header. In order to find these bytes, the reading module 640 skips over the data and reads the desirable information. Thus, this module can extract information related to the name of the object, its dimensionality, and information about how the data itself is stored on disk.

The reading module 640 also extracts information from subheaders. After the reading module 640 receives information related to the dimensionality of the object, it locates the subheader of the dimension of interest. Each subheader defines the coordinates of a vector in multidimensional space and the number of points along the vector. The data along this vector can be regularly or irregularly spaced.

Figure 7:
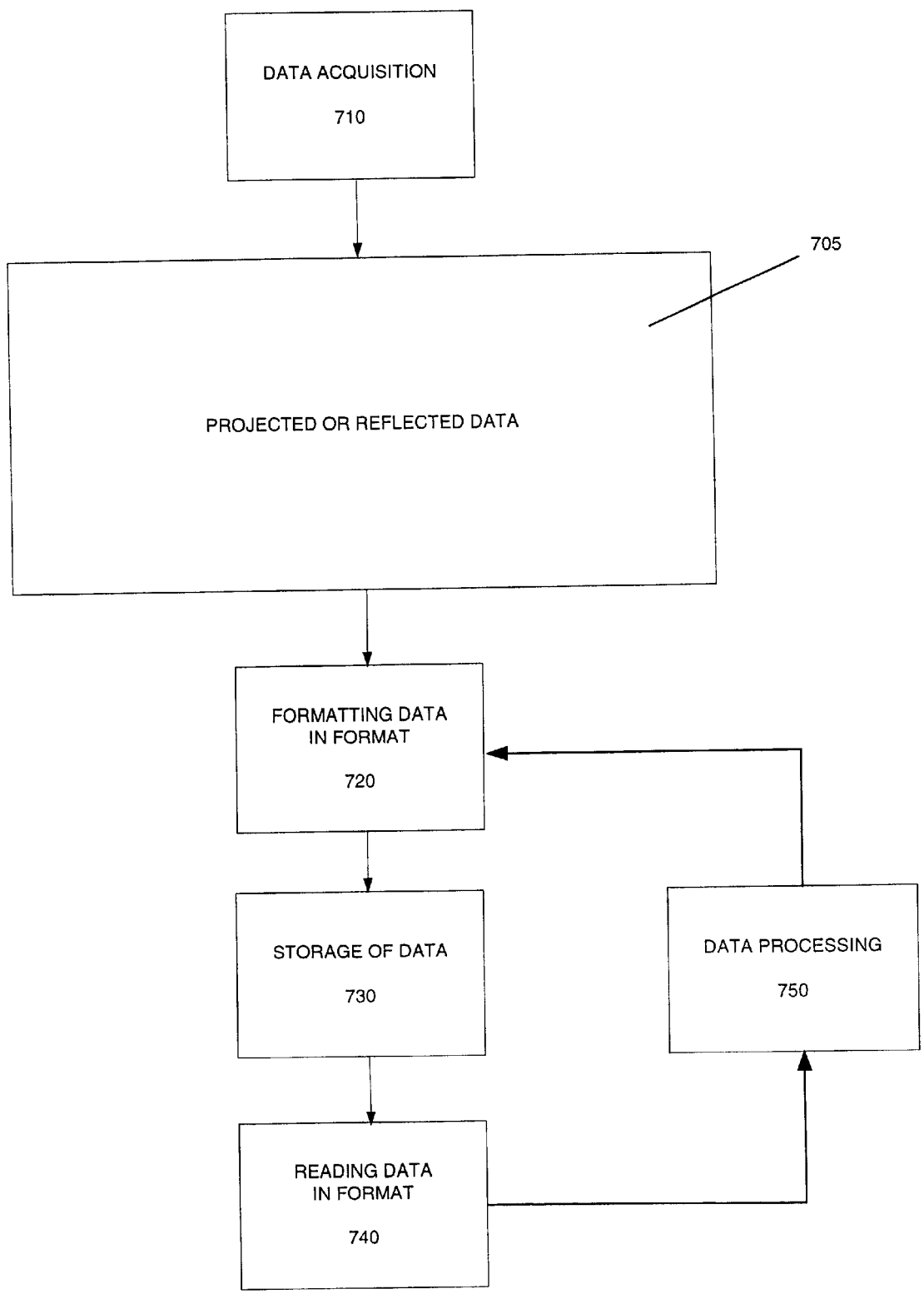
FIG. 7 is a block diagram of one embodiment of a process for manipulating and processing data using the system of FIG. 1A.

FIG. 7 is a block diagram illustrating the process of acquiring, formatting, storing, reading, and processing data where the data extends in several dimensions. The data is formatted in the file format 500. The process illustrated in FIG. 7 begins with the acquisition 710 of a data set, e.g., projected or reflected data set 705. The process formats 720 the data in format 500. The formatted data is then stored 730. The system can efficiently read 740 the stored data and process 750 the data.

With reference to FIG. 7, after the system extracts the data from format 500, the system processes 750 the extracted data. The system can display the data on a monitor, Video Graphic Array (VGA) or flat panel screen; or it can store the data in a permanent storage medium, such as a disk, or a tape. Referring back to FIGS. 3–4, note that the processing can also including utilizing the sensor point location and focal point data to form correspondences between images for a depth map to form new images of the object, i.e., a three-dimensional image of the object.

Figure 8:
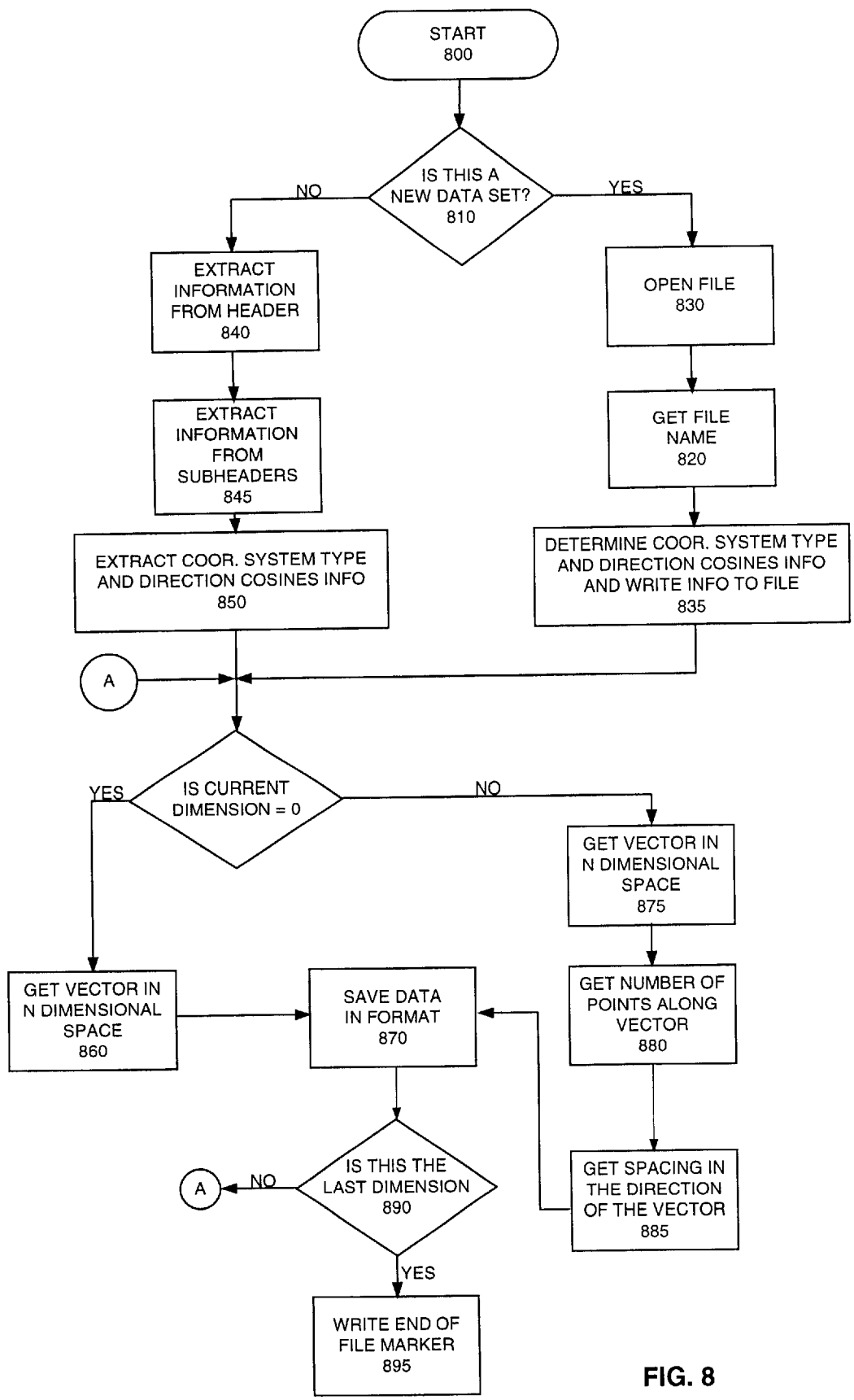
FIG. 8 is a flow chart diagram illustrating one embodiment of a process for saving data using the system of FIG. 1A.

FIG. 8 is a flow chart diagram illustrating one embodiment of a process for storing data in n-dimensional format 500. Modules in the memory unit 620 of FIG. 6 perform the process of FIG. 8. The process starts 800 by determining whether acquired data represents a new data set or is additional data for an existing data set 810. If the current data set is a new data set, the process opens a file 830 and associates a file name 820 with the new file.

In the alternative, if the data set is additional data for an existing data file, the process extracts information from a file header 840. This information may contain data type, the name of the format, and the number of possible dimensions in the file. A file header structure is shown in FIG. 5. Then, the process extracts information from subheaders 845. The system performs steps 840 and 845 so that the system can add data to an existing file without changing the structure of data previously entered in the file.

Regardless of whether the data set is a new data set or additional data to be added to an existing data set, the process next determines whether the current dimension is zero 855. In other words, the process determines if the portion of the data that is being read refers to a point, i.e., the reference point value and direction. If the current dimension is zero, the process obtains coordinates of a vector in a multidimensional space 860 to indicate the direction of the reference point relative to a global coordinate system.

Each data file starts with a reference point, which represents the starting point of a multidimensional data volume. Coordinates of this point are given in the basic or global coordinate system. That is, when the current dimension is zero, part of the data set corresponding to the zero dimension data consists of one reference point A(0). Finally, the process saves the zero-dimensional data in the n-dimensional format 870. As noted above, data can be stored in a storage device 630, a memory 620, or a permanent storage medium, such as a disk, or a tape.

In contrast, if the current dimension is not zero, the coordinate system of the data set in question has at least one dimension. The process obtains a vector in multidimensional space 875 representing the direction of the dimension in question relative to the preceding dimension, obtains the number of points, N, 880 and obtains spacing in each coordinate, $\Delta X^i$, 885 for regularly spaced data, where i represents a dimension number. Finally, the process saves the data in the n-dimensional format 870.

The process then determines whether the data represents the last dimension 890. If the data represents the last dimension, the process writes the end of the file marker 595. In the alternative, if the data does not represent the last dimension, the process loops back to 855 to determine whether the current dimension is zero.

Figure 9:
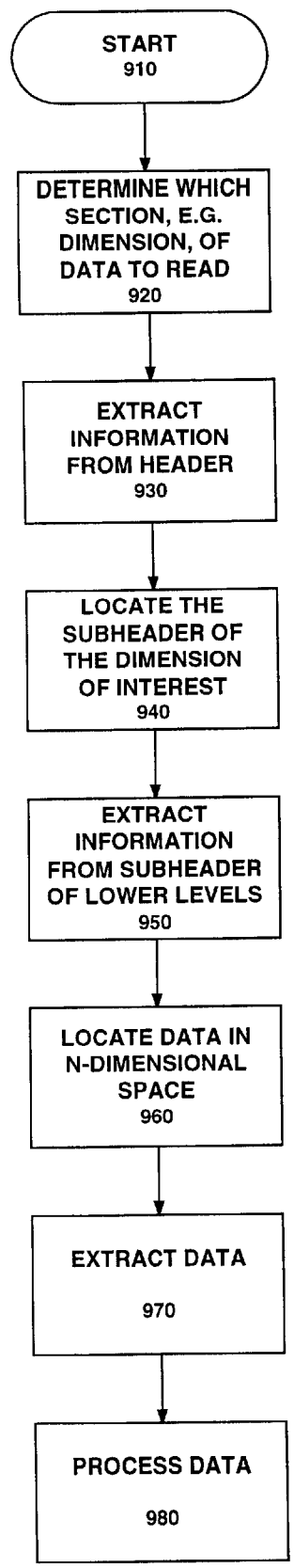
FIG. 9 is a flow chart diagram illustrating one embodiment of a process of reading data in an n-dimensional format using the system of FIG. 1A.

FIG. 9 is a flow chart diagram illustrating one embodiment of a process for reading data saved in n-dimensional format 500. This process is performed by at least one module in the memory unit 620 of FIG. 6. The process starts 910 by determining which data needs to be read 920. Then, the process extracts information from a file header 930. One embodiment of the file header consists of a series of blocks including a file identifier, a format identifier, a data type identifier, and a number of dimensions field. The type of the data and number of dimensions are stored in the last two bytes of the file header. The size of every dimension is in the last byte of the corresponding header. In order to find these bytes, the file reading process skips over the data and reads the desirable information related to the name of the object, its dimensionality, and information about how the data itself is stored.

Once the process determines the number of dimensions, the process locates the header of the dimension of interest (a subheader) 940 and extracts information from the subheader of a lower dimension 950. Next, the process locates data in multidimensional space 960 described in a particular subheader and extracts the data 970. Finally, after the data has been extracted from the file header and subheader, it is processed 980. Referring to FIG. 1A, a system 126 can display the processed data on a monitor, a Video Graphic Array (VGA) or a flat panel screen; and/or it can be stored in a storage device 630, a memory 620, or a permanent storage medium, such as a disk, or a tape.

Referring again to FIG. 1A, it will be understood that the system and n-dimensional data format of the present invention facilitates formatting projected or reflected data into a format that that may be fused with other types of data, including data sets (e.g., CT data) collected in different coordinate systems and having other attributes. In particular, format 500 permits sufficient data to be stored to permit depth maps to be later calculated by the workstation from stored projected or reflected data so that new images (e.g., 3-D images) may be calculated from different viewpoints and fused with other types of images.

The above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the present invention.

What is claimed is:

1. A computer implemented method for storing formatted image data corresponding to a projected image of an object, wherein said projected image is obtained by projecting x-rays from an x-ray source through the object to a sensor which records the projected image, said method comprising the steps of:

formatting the image data by providing a file header, a reference point value field which defines the location of the sensor, and a focal point value field which defines the location of x-ray emission from the x-ray source, and storing the formatted image data to a storage medium accessible by a computer.

2. The method of claim 1, wherein the format further comprises: a transformation field, and a type of the coordinate system.

3. The method of claim 1, wherein coordinates of the focal point are stored in a local coordinate system.

4. The method of claim 1, wherein the format includes at least two dimensions for storing image data.

5. The method of claim 1, further comprising the steps of:

acquiring second image data of the object;

formatting the second data; and fusing the first and second image data into a three-dimensional image of the object, based on respective values of the reference point value fields and the focal point value fields.

6. The method of claim 5, wherein the step of fusing the first and second data sets includes the step of: forming a depth map for the data image data.

7. The method of claim 1, wherein the second image data is reflected image data of the object.

8. The method of claim 4, further comprising a reference point value field and a focal point value field for data of each dimension.

9. A computer apparatus for formatting, image data corresponding to a projected image of an object, wherein aid projected image is obtained by projecting x-rays from an x-ray source through the object to a sensor which records the projected image, the computer apparatus comprising:

a central processing unit (CPU); and a memory unit storing code executed by the CPU, said memory unit storing code comprising:

a formatting module configured to format the image data by providing a filer header, a reference point value field which defines the location of the sensor, and a focal point field which defines the location of x-ray emission from the x-ray source; and a storage module in communication with the formatting module and configured to store the formatted image data.

10. The computer apparatus of claim 9, wherein the formatting module is configured for formatting second image data of the same object, wherein the second image is reflected image data of the object.

11. The computer apparatus of claim 10, further comprising a fusing module for fusing the first and second image data.

12. The computer apparatus of claim 9, wherein the format includes at least two dimensions for storing image data.

13. The computer apparatus of claim 9, wherein the formatting module further provides a header of the reference point, and a header of the focal point.

14. The computer apparatus of claim 9, wherein the image data is described using a non-Cartesian coordinate system.

15. The computer apparatus of claim 9, wherein the image data is described using a Cartesian coordinate system.

16. A computer-readable medium containing a computer program for formatting image data corresponding to a projected image of an object, wherein said projected image is obtained by projecting x-rays from an x-ray source through the object to a sensor which records the projected image, the computer program comprising:

executable code stored in a memory unit;

a formatting module configured to format the image data by providing a file header, a reference point value field which defines the location of the sensor, and a focal point value field which defines the location of x-ray emission from the x-ray source; and a storage module in communication with the formatting module and configured to store the formatted image data.

17. The computer readable medium of claim 16, wherein the formatting module configured to format second image data into a compatible file structure, whereby the first and second image data may be fused.

18. The computer readable medium of claim 16, wherein the format further comprises a transformation field and a type of the coordinate system field.

19. The computer readable medium of claim 16, wherein the format further comprises at least two dimensions for storing two-dimensional image data.

* * * * *

UNITED STATES PATENT AND TRADEMARK OFFICE
CERTIFICATE OF CORRECTION

PATENT NO. : 6,690,762 B1
DATED : February 10, 2004
INVENTOR(S) : Alexander L. Berestov It is certified that error appears in the above-identified patent and that said Letters Patent is hereby corrected as shown below:

<u>Column 6,</u>
Line 42, "(x, Y Z)" should read -- (X, Y, Z) --; and

Line 56, "x is" should read -- $\vec{x}$ is --.

<u>Column 8,</u>
Line 18, "y=t11X" should read -- y=t21X --.
Line 20, "z=t11X" should read -- z=t31X --; and
Line 31, "a a second" should read -- a second --.

<u>Column 9,</u>
Line 53, "including" should read -- include --.

<u>Column 11,</u>
Line 4, "format that" should read -- format --;
Line 50, "data image data" should read -- image data --;
Line 56, "formatting," should read -- formatting --; and
Line 57, "aid" should read -- said --.

Signed and Sealed this

Twenty-first Day of September, 2004

JON W. DUDAS
*Director of the United States Patent and Trademark Office*